(12) United States Patent
Shaw et al.

(10) Patent No.: US 8,048,031 B2
(45) Date of Patent: Nov. 1, 2011

(54) IV CATHETER INTRODUCER

(75) Inventors: Thomas J. Shaw, Frisco, TX (US); Ni Zhu, Plano, TX (US); Kathryn Margaret Duesman, Pilot Point, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

(21) Appl. No.: 12/464,555

(22) Filed: May 12, 2009

(65) Prior Publication Data

US 2010/0168674 A1    Jul. 1, 2010

(51) Int. Cl.
*A61M 5/178* (2006.01)
(52) U.S. Cl. ......... 604/164.07; 604/164.08; 604/164.12; 604/263
(58) Field of Classification Search ............. 604/164.01, 604/110, 192, 198, 164.07–164.08, 164.12, 604/263
See application file for complete search history.

(56) References Cited

U.S. PATENT DOCUMENTS

| | | | |
|---|---|---|---|
| 4,553,962 A * | 11/1985 | Brunet | 604/198 |
| 4,747,831 A | 5/1988 | Kulli | |
| 4,828,548 A | 5/1989 | Walter | |
| 4,973,313 A * | 11/1990 | Katsaros et al. | 604/165.02 |
| 5,129,884 A | 7/1992 | Dysarz | |
| 5,501,675 A | 3/1996 | Erskine | |
| 5,746,215 A | 5/1998 | Manjarrez | |
| 5,817,058 A | 10/1998 | Shaw | |
| 5,989,220 A | 11/1999 | Shaw et al. | |
| 6,083,202 A | 7/2000 | Smith | |
| 6,090,078 A | 7/2000 | Erskine | |
| 6,096,005 A | 8/2000 | Botich et al. | |
| 6,494,863 B1 | 12/2002 | Shaw et al. | |
| 6,872,193 B2 * | 3/2005 | Shaw et al. | 604/164.07 |
| 2008/0215009 A1 | 9/2008 | Shaw et al. | |

* cited by examiner

*Primary Examiner* — Theodore Stigell
(74) *Attorney, Agent, or Firm* — Locke Lord Bissell & Liddell, LLP

(57) ABSTRACT

An IV catheter introducer having an elastomeric grommet disposed between the housing and the IV catheter assembly that helps avoid unintentional separation of IV catheter assembly from the housing during shipping and handling prior to use, that acts as a needle guide, that helps align the housing and IV catheter assembly coaxially, that indicates that top side of the catheter introducer, that provides proper rotational alignment between the grommet and housing, that wipes blood off the needle during withdrawal of the needle from the catheter assembly and grommet, that impedes blood flow out of the catheter hub after needle withdrawal, and that assists the user in separating the housing from the IV catheter assembly following insertion of the catheter and withdrawal of the needle.

11 Claims, 7 Drawing Sheets

IV CATHETER INTRODUCER

BACKGROUND OF THE INVENTION

1. Field of the Invention

The invention is a medical device, optionally having a retractable needle, that is used to insert a catheter into a patient's body, especially for the intravenous delivery of a fluid. The subject invention prevents reduces the likelihood of spilling blood following withdrawal of the needle, and also reduces the likelihood of needlestick injuries or pathogenic contamination to medical personnel and others.

2. Description of Related Art

Intravenous ("IV") catheter insertion devices are well known. When a catheter is inserted into a patient for the intravenous delivery of a fluid, a disposable needle passing through the catheter is utilized to puncture a vein to permit entry of the catheter. The needle is then withdrawn, leaving the catheter in place for connection to an IV bag or bottle, or to be capped for later use.

In recent years, because of the prevalence of blood-borne pathogens such as HIV and hepatitis, there has been an increasing need for catheter introducers that prevent accidental needle stick injuries to medical personnel and to other employees who handle trash, laundry or other refuse containing used needles. As a result, new products have been designed that incorporate special needle covers or mechanisms for retracting the needle following use. Such devices are disclosed, for example, in U.S. Pat. Nos. 4,747,831; 4,828,548; 5,129,884; 5,501,675; 5,746,215; 5,817,058; 5,989,220; 6,083,202; 6,090,078; and 6,096,005. Some of the prior art devices contain numerous complicated parts that substantially increase manufacturing costs and interfere with the user's ability to feel when the needle is properly inserted into the patient. Other devices require two-handed operation or are prone to premature needle retraction during shipment, storage and handling.

More recently, U.S. Pat. No. 6,872,193, a patent from which the subject application claims priority, issued to the present applicants. Notwithstanding the many benefits and advantages achieved with the apparatus disclosed in that patent, applicants have now invented a new device having some structural features in common with those patented in U.S. Pat. No. 6,872,193 but also embodying additional structural elements. The newly added elements enable additional functional advantages beyond those readily achievable using the apparatus of the prior invention.

As with the IV catheter introducer previously disclosed, the apparatus comprising features newly disclosed herein can be manufactured economically and reliably at high speed, will not retract the needle prematurely, can be operated with one hand, and will better protect the user and others from accidental sticks and exposure to blood-borne pathogens.

SUMMARY OF THE INVENTION

According to one embodiment of the invention, the IV catheter introducer as newly disclosed herein preferably comprises a housing, a plunger having one end slidably insertable into the housing, a needle assembly with a tubular needle holder attachable to a forwardly extending portion of the plunger, an IV catheter assembly and an elastomeric grommet disposed between the housing and the IV catheter assembly. The elastomeric grommet, preferably made of rubber, keeps the hub of the IV catheter assembly from separating from the housing during shipping and handling prior to use, identifies the top side of the device relative to the needle bevel, and provides an upwardly extending tab that is used for the application of digital pressure when inserting the catheter into the vein and when separating the housing from the grommet and hub. The elastomeric grommet has a thin web that is pierced by the needle during assembly. The web wipes blood off the outside surface of the needle during needle withdrawal and impedes blood flow out of the catheter hub and grommet after needle withdrawal and prior to connection of the hub to another device.

According to another embodiment of the invention, the subject IV catheter introducer comprises the foregoing features in combination with retraction spring that retracts the needle into the housing and plunger assembly following use. When used with a retractable needle, the thin web of the elastomeric grommet also dampens the retraction force to reduce the likelihood of forward splattering during retraction.

According to another embodiment of the invention, a rearwardly facing projection is provided on the back side of the elastomeric grommet to facilitate a preferred rotational alignment of the grommet with a notch in the perimeter of the forwardly facing flange of the housing.

According to another embodiment of the invention, the IV catheter introducer comprises a pair of opposed, longitudinally extending wings, most preferably having raised finger pads.

The IV catheter introducers of the invention have few parts, can be manufactured reliably at high speed, significantly reduce the likelihood of premature needle retraction during storage and handling, are easily usable in one hand, and will protect medical and other ancillary personnel from accidental needle sticks and the possibility of resultant infection by blood-borne pathogens Use of the present invention also affords significant economic benefits to health care providers and insurers through reduced testing and follow-up costs.

BRIEF DESCRIPTION OF THE DRAWINGS

The apparatus of the invention is further described and explained in relation to the following figures of the drawing wherein.

DETAILED DESCRIPTION OF PREFERRED EMBODIMENTS

Figures 1, 4, 5, 6:
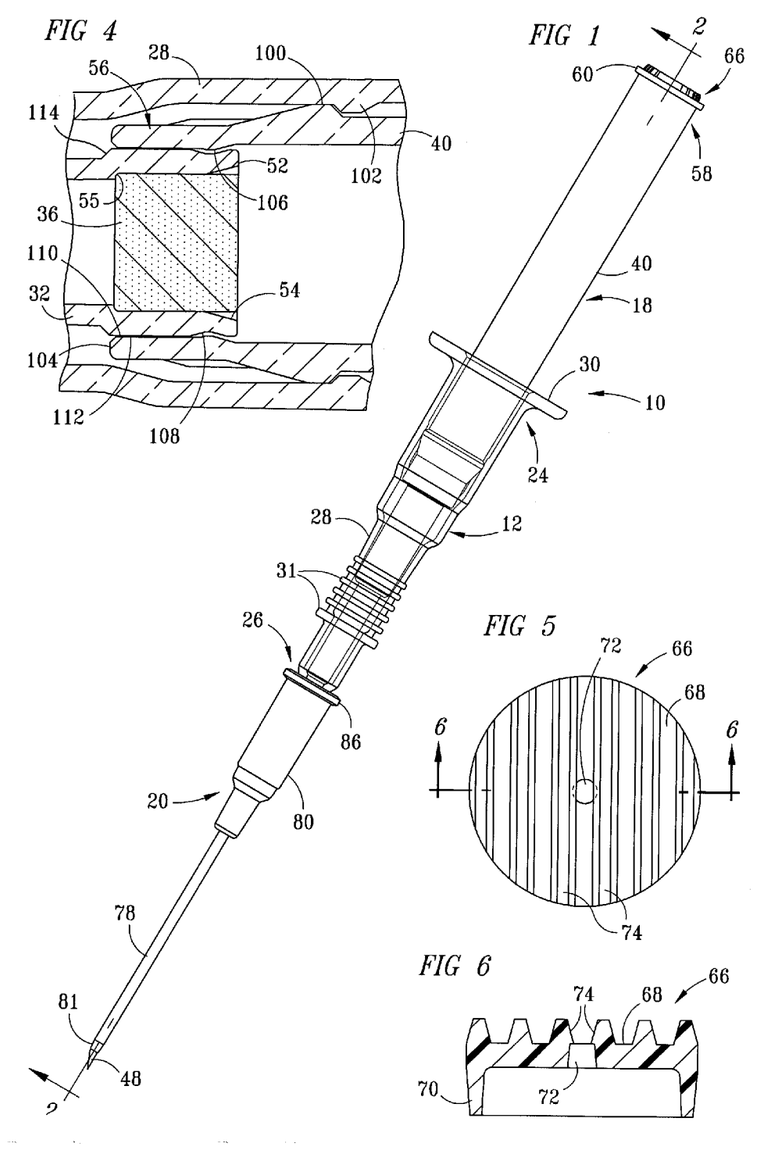
FIG. 1 is a simplified perspective view of a preferred IV catheter introducer of the invention as depicted in U.S. Pat. No. 6,872,193, with the catheter needle ready for use.
FIG. 4 is an enlarged detail view taken from FIG. 2, and depicts the detent structure holding the landed front opening of the plunger tube in the desired position relative to the retractable needle holder prior to retraction.
FIG. 5 is an enlarged plan view of the vented plunger end cap.
FIG. 6 is a cross-sectional elevation view taken along line 6-6 of FIG. 5.
Figure 2:
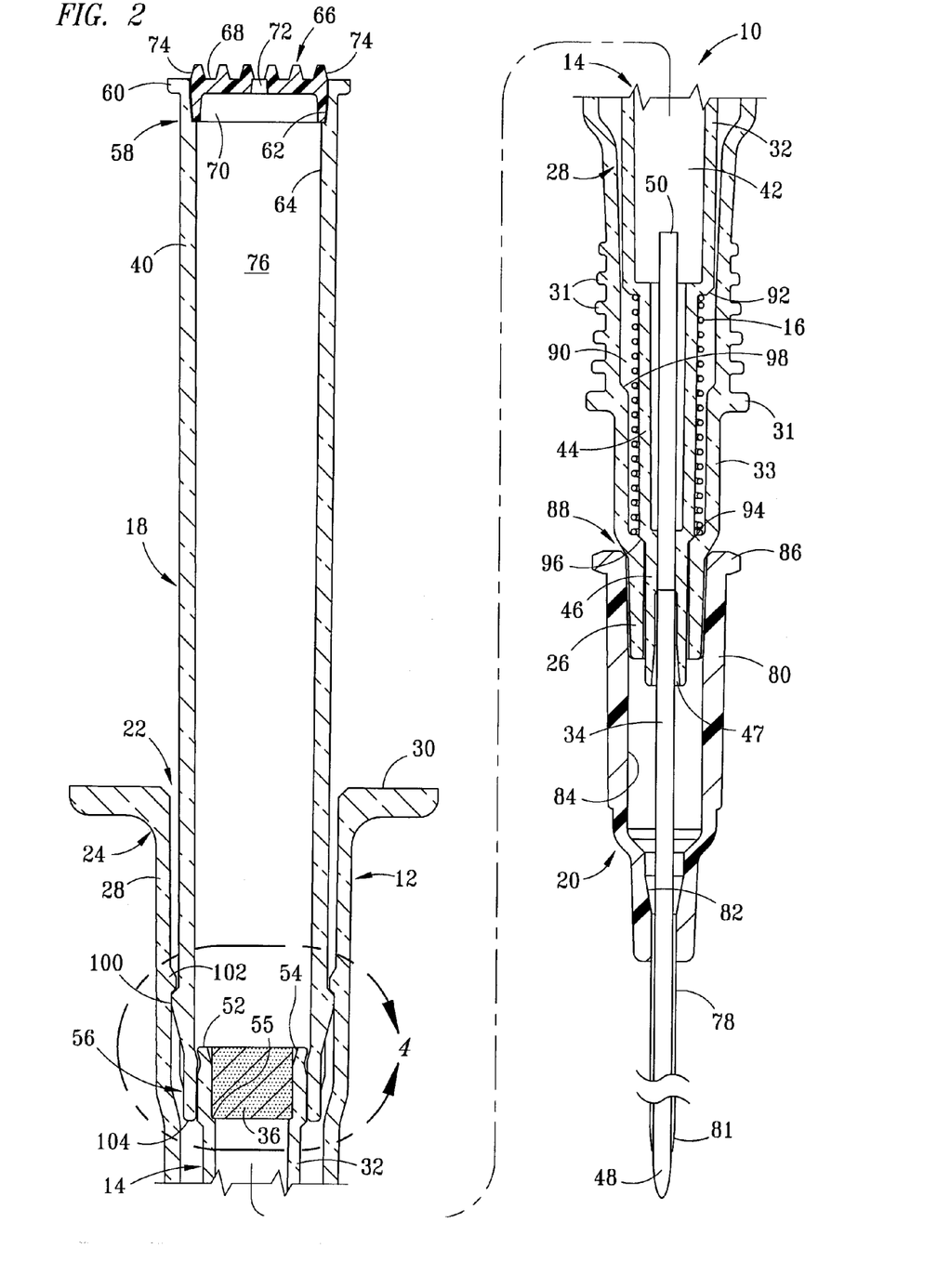
FIG. 2 is an enlarged, cross-sectional elevation view taken along line 2-2 of FIG. 1.

Referring to FIGS. 1-2, IV catheter introducer 10 preferably comprises tubular plastic housing 12, needle holder assembly 14, retraction mechanism 16, plunger assembly 18 and IV catheter 20. Plastic housing 12 has an internal bore 22 that narrows progressively between open end 24 and reduced diameter tip 26, except for a short distance below inwardly projecting annular ring 102, as described below. Plastic housing 12 is preferably injection molded from a substantially transparent polymeric resin such as polycarbonate to permit easy viewing through sidewall 28. The outside diameter of housing 12 generally follows the tapered narrowing of internal bore 22, so that sidewall 28 has a substantially constant thickness except where it flares outwardly to form laterally extending wings 30 and to provide a longitudinally spaced series of annular ridges 31 nearer to tip 26 to create a textured gripping area for the fingers of the user.

Needle holder assembly 14 is retractably mounted within the lower portion of housing 12 and preferably comprises a tapered, elongate tubular body 32, needle 34 and porous plug 36. Body 32 of needle holder assembly 14 is preferably injection molded from a substantially transparent polymeric resin such as polycarbonate and comprises a tapering sidewall of substantially constant thickness that further defines flash chamber 42, spring guide section 44 and needle support section 46, each of which has a progressively smaller diameter. Tubular body 32 of needle holder assembly 14 is desirably shaped so as to permit needle holder assembly 14 to be inserted into sliding engagement with housing 12 during assembly, as described in greater detail below. The upper end portion of tubular body 32 is adapted to releasably engage lower end 56 of plunger assembly 18 as described below in relation to FIG. 4. As viewed in FIG. 2, retraction mechanism 16, which is preferably a spring, is confined within annular space 90 between housing 12 and spring guide section 44 of tubular body 32, and is held in compression between downwardly facing shoulder 92 of tubular body 32 and upwardly facing shoulder 94 of housing 12. Although this embodiment uses a compressed spring that exerts a retraction force by expanding, other similarly effective means such as an extension spring can likewise be used to retract the needle.

Needle 34 is hollow and has a beveled end 48, which is inserted into a patient's vein during use, and a blunt end 50 that extends into flash chamber 42. A longitudinally extending bore provides fluid communication through needle 34 between beveled end 48 and blunt end 50. Needle 34 is preferably insert molded into needle support section 46 of tubular body 32 to create an insert molded needle. However, needle 34 can be glued or sonically welded into body 32 if desired. A tapered needle insertion opening 47 is desirably provided at the lower end of needle support section 46 if needle 34 is to be inserted after molding needle support section 46. By using a needle 34 that is long enough to extend into flash chamber 42, the bore of needle 34 will not become occluded during insert molding. Also, because a minor amount of blood flows upwardly through needle 34 into flash chamber 42 whenever needle 34 is introduced into the vein of a patient, making blunt end 50 visible in flash chamber 42 permits the user to view blood as soon as it enters flash chamber 42, confirming to the user that needle 34 is properly positioned inside the vein.

At the top of flash chamber 42 of needle holder assembly 14, end 52 of tubular body 32 is blocked with porous plug 36 that frictionally engages the walls of annular recess 55 in body 32. The insertion of porous plug 36 into tubular body 32 is preferably made easier by tapered inside wall 54 adjacent to end 52. Porous plug 36 is preferably made of any suitable porous material that will allow air to be displaced out of needle 34 and flash chamber 42 by blood rising through needle 34 following insertion into a vein, but will prevent any such minor amount of blood from exiting flash chamber 42. A significant advantage of IV catheter introducer 10 disclosed herein is that flash chamber 42 is visible through only two layers of clear plastic: the transparent wall of tubular body 32 around flash chamber 42; and the transparent wall of housing 12. With many devices disclosed in the prior art, the user must peer through three or more plastic layers to view the flash chamber, making it more difficult to observe when blood begins entering the chamber.

Plunger assembly 18 preferably comprises a polymeric plunger tube 40 having a substantially cylindrical sidewall with a lower end portion 56 that is proximal to end 52 of tubular body 32 of needle holder assembly 14, and an upper end portion 58 that projects longitudinally outward from open end 24 of housing 12. Plunger tube 40 is preferably injection molded from a polymeric resin, and most preferably, from a substantially transparent polymer such as polycarbonate. Lower end portion 56 of plunger assembly 18 releasably engages tubular body 32 of needle holder assembly 14 and cooperates with needle holder assembly 14 to form the detent structure of the invention as described in greater detail below in relation to FIG. 4. Upper end portion 58 of plunger tube 40 preferably comprises a small, radially extending annular flange 60 surrounding a tapered annular recess 62 in surface 64 that receives and frictionally engages end cap 66, which is further described and explained in relation to FIGS. 5 and 6. With IV catheter introducer 10 prepared for use, upper end 58 of plunger assembly 18 desirably extends from about 1.5 to about 3 inches from housing 12 so that upper end 58 can be nestled against the palm of the hand while the user's fingers grip wings 30 or annular ridges 31 of housing 12 to facilitate one-handed operation. Pulling back on housing 12 with the fingers triggers retraction of needle holder assembly 14, as discussed below in relation to FIG. 3.

Referring to FIGS. 5 and 6, end cap 66 is preferably molded from a polymeric resin and, most preferably, from a resin that is pigmented in a color chosen to correspond to the gauge of needle 34, shown in FIGS. 1-2, to assist users in readily differentiating among IV catheter introducers 10 having different sized needles. End cap 66 preferably further comprises a substantially continuous, circular end wall 68 connected to a longitudinally extending annular skirt 70 that is inwardly tapered to provide contacting frictional engagement with annular recess 62 of plunger tube 40 as previously described. It should be understood that there are many ways of engaging end cap 66 into upper end portion 58 of plunger tube 40. End cap 66 may be glued, snapped-on, sonically welded, dual shot molded or engaged by any other similarly effective means. Dual shot molding refers to any molding process that allows different materials or different colored materials to be molded concurrently. Vent hole 72 is preferably centrally disposed in end wall 68 and is desirably surrounded by surface relief features such as a plurality of outwardly extending molded ribs 74 that extend across surface 68. Ribs 74 are preferably of sufficient number, spacing and height that vent hole 72 is not blocked by the hand of the user, even when part of the hand is placed over end cap 66 during operation of IV catheter introducer 10. Vent hole 72 is preferably large enough to rapidly vent the volume of air displaced from retraction cavity 76 when needle holder assembly 14 is retracted into plunger tube 40 following insertion of the catheter.

Referring again to FIGS. 1-2, IV catheter 20 preferably includes a flexible rubber or plastic cannula 78 and a hub 80 having a needle channel 82 and a tubular section 84 with an annular flange 86 defining an opening 88 having a diameter such that opening 88 will receive and frictionally engage tip 26 of housing 12. At the end of cannula 78 is an inwardly tapered end 81 that provides an interference fit near beveled end 48 of needle 34. During the attachment of hub 80 to tip 26, needle 34 is inserted through flexible cannula 78 and inwardly tapered end 81, with beveled end 48 extending slightly beyond the inwardly tapered end 81. The inside diameter of cannula 78 is preferably slightly greater than the outside diameter of needle 34 to permit easy retraction of needle 34 through cannula 78 following insertion. Hub 80 is preferably also adapted for easy connection to a convention IV tubing connector following retraction of needle 34 and removal of tip 26 from tubular section 84 of hub 80.

Referring to FIG. 2, IV catheter introducer 10 of the invention is preferably assembled by dropping retraction spring 16 through opening 22 into housing 12. Retraction spring 16, which is a coil spring biased against compression, preferably has a diameter that causes it to seat just above inclined annular shoulder 94 inside housing 12, where it is supported in substantially vertical alignment by section 33 of sidewall 28. Pre-manufactured needle holder assembly 14 is then inserted downwardly through open end 22 of housing 12, with beveled end 48 of needle 34 passing downwardly through retraction spring 16 and tip 26 of housing 12, until inclined annular shoulder 96 of tubular body 32 abuts against shoulder 94 of housing 12. Alternatively, spring 16 can be placed over needle holder assembly 14 prior to insertion of needle holder assembly 14 into housing 12. Also, if desired, needle 34 can be glued or sonically welded into needle holder assembly 14 after needle holder assembly 14 is inserted into housing 12. Inclined annular shoulder 92 of tubular body 32 preferably will not contact inclined annular shoulder 98, to permit shoulder 96 to seat properly against shoulder 94.

Referring to FIGS. 2 and 4, lower end portion 56 of pre-manufactured plunger assembly 18 is next introduced into housing 12 through opening 22. As plunger tube 40 travels downwardly into housing 12, nose 104 of plunger tube 40 reaches and slides over end 52 of tubular body 32 of needle holder assembly 14. When nose 104 reaches end 52, radially extending annular boss 100 on plunger tube 40 is still disposed above inwardly projecting annular ring 102 of housing 12, and the inside diameter of plunger tube 40 at nose 104 is sufficiently greater than the outside diameter of end 52 to permit lower end portion 56 of plunger tube 40 to slidably engage the portion of tubular body 32 that is adjacent to end 52. As plunger assembly 18 is inserted farther into housing 12, annular boss 100 engages and overrides annular ring 102. Annular ring 102 then resists rearward movement of plunger tube assembly 18 and combined needle holder assembly 14 once they are installed in the housing with the needle extended for use. If there is an attempt to withdraw the plunger tube assembly 18 from housing 12, the shoulder of annular boss 100 will contact the shoulder of annular ring 102 and prevent the withdrawal unless there is an exertion of substantial force. However, it should be understood that annular ring 102 is desirably sufficiently small to allow for the withdrawal of a molding tool during the manufacturing process. Referring to FIG. 4, a detail view taken from FIG. 2, plunger tube 40 continues to slide downwardly over tubular body 32 of the needle holder assembly until inwardly facing annular boss 106 on the inside surface of lower end portion 56 reaches and snaps into engagement with cooperatively sized and aligned, outwardly facing annular recess 108 of tubular body 32. Referring to FIGS. 2 and 4, the configuration and dimensions of annular boss 106 and annular recess 108 cause boss 106 to be biased radially inward into annular recess 108.

It should be understood that boss 106 on the inside of plunger tube 40, is not required to be circumferentially coextensive with annular recess 108 of tubular body 32. Thus, for example, boss 106 can instead comprise a circumferentially spaced array of discrete, inwardly extending bumps that are biased into engagement with recess 108. It is preferred, however, that recess 108 extend completely around tubular body so that the slidable engagement between plunger tube 40 and tubular body 32 does not require a specific rotational alignment between the two parts. The configuration and dimensions of boss 106 and recess 108 are preferably such that the force required to slidably disengage boss 106 from recess 108 by forcing plunger tube 40 farther down into housing 12 is greater than the biasing force being exerted against needle holder assembly 14 by compressed retraction spring 16 and by the additional force that is exerted upwardly on the needle 34 during catheter insertion procedures. IV catheter 20 can be assembled to tip 26 of housing 12 prior to the insertion of needle holder assembly 14 and plunger assembly 18 into housing 12. Alternatively, plunger assembly 18 and needle holder assembly 14 (sometimes referred to as a needle support assembly) can also be assembled to each other prior to insertion into housing 12. The frictional engagement between boss 106 and recess 108 when they are cooperatively engaged is preferably sufficient to permit needle holder assembly 14 and plunger assembly 18 to be inserted together into housing 12.

Beveled needle end 48 and a portion of cannula 78 are desirably inserted into a patient's vein while grasping annular ridges 31 of housing 12 with the thumb and fingers. Following insertion of the catheter into a patient, needle holder assembly 14 is retracted by grasping wings 30 or annular ridges 31 with one's fingers, or thumb and fingers, and then using the palm or heel of the hand against end cap 66 to force plunger tube 40 farther down into housing 12. When this occurs, the frictional engagement between boss 106 and recess 108, as seen in FIG. 4, is over-pressured, causing boss 106 to ride up onto surface 112 of tubular body 32. Continued downward movement of plunger tube 40 relative to tubular body 32, which is firmly seated against housing 12, causes boss 106 to drop off inclined shoulder 114 of tubular body 32. When this occurs, there is no remaining significant frictional force being exerted against compressed retraction spring 16, and spring 16 rapidly expands, causing needle holder assembly 14 to be propelled upwardly into retraction cavity 76, simultaneously withdrawing needle 34 at least to a position where beveled end 48 is withdrawn into housing 12.

Figure 3:
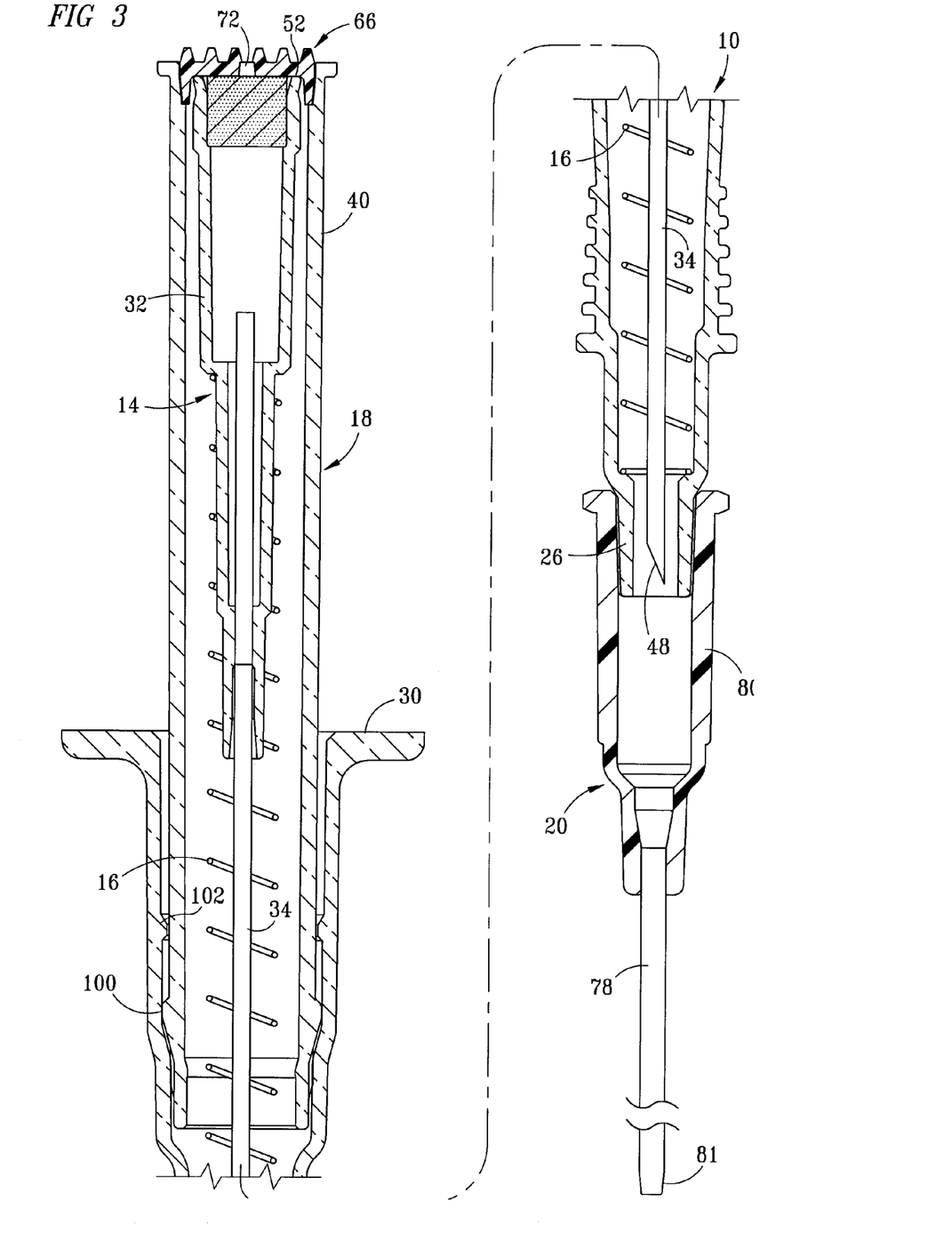
FIG. 3 is a view as in FIG. 2, but with the needle retracted following use.

Referring to FIG. 3, retraction spring 16 is fully expanded and top end 52 of needle holder assembly 14 is at least partially withdrawn into retraction cavity 76. Air previously present in retraction cavity 76 of plunger tube 40 has been vented through vent hole 72 as needle holder assembly 14 moved upwardly within the cavity in response to expansion by retraction spring 16. Top end 52 of needle holder assembly 14 has moved upward within retraction cavity 76 sufficiently that beveled end 48 of needle 34 is withdrawn into housing 12. When needle 34 is in the position shown in FIG. 3, tip 26 of housing 12 can be safely detached from IV hub 80.

The improved IV catheter introducer of the invention is well suited for automated manufacture and assembly. Aside from the catheter, needle and spring, only a housing, retractable needle holder and a capped, vented plunger tube are needed. Although housing 12 can be made in a straight configuration with a straight internal wall, it is preferably made with a stepped configuration that, with the exception of the lower shoulder of annular ring 102, tapers inwardly from top to bottom. This taper makes it easy to withdraw a core mandrel used in the molding process. Although not illustrated in the drawings, it should be understood that beveled end 48 of needle 34 is preferably protected during the manufacturing process, shipping and storage by a tubular cover that slides upwardly over the outside of cannula 78, preventing the needle from being damaged.

An important aspect of the subject IV catheter introducer is the fact that the operator can conveniently operate the retractable introducer structure with one hand. One handed operation is possible because the plunger tube desirably extends about 1.5 to about 3 inches past where the wings of the housing are located. This allows force to be applied against the plunger tube by the fleshy part of the palm while using the fingers behind the wings or the annular ridges of the housing to resist the force and smoothly initiate retraction. The other hand remains free to grasp the hub of the catheter. Timing for freeing the hub from the introducer device and attaching an IV tube to the hub is under complete control of the operator. In one motion, the hub of the catheter can be separated from the insertion device, which can then be safely set aside while the connection is then made to the IV tube or other device that is to be connected to the patient. The catheter introducer can be safely set aside without concern onto a bed or tray, because the needle has already been safely retracted before the catheter assembly is disconnected from the housing. When the fingers pull back on the wings or annular ridges of the housing to trigger retraction, the operator can both hear and see that the needle is safely retracted and immediately disengage and safely set aside the device to free his hand for use in making the necessary IV connection before loss of fluid from the patient occurs.

The IV catheter introducer of the invention does not have to resist as much force imposed by the needle on the retraction parts as does a conventional syringe that is required to puncture a rubber seal commonly used on vials. Consequently, the retractable parts need only be able to resist the force encountered during normal clinical use without retracting. With the apparatus disclosed herein, dimensional tolerances and differential thermal expansion rates are less critical than with devices where the only frictional engagement is provided by surface-to-surface contact between smooth facing surfaces.

The IV catheter introducer disclosed herein is less likely to retract the needle prematurely than prior art devices, even when subjected to rough handling and widely varying temperatures and humidity during shipment and storage prior to use. The invention has a simple, streamlined shape and a retraction spring that is simpler to operate and more reliable than others previously used. The device can be operated with one hand in any rotational position where the wings are accessible because it has no external latches that require placing the device in a particular orientation. Further, the wings prevent the catheter introducer from rolling when placed on an oblique surface. With the device held in the hand, the retraction force is applied linearly along the main longitudinal axis. A very short stroke movement is sufficient to trigger retraction. Successful retraction is noted both visually and audibly because the operator can easily see the retracted parts in the housing and retraction creates an unobtrusive noise.

Another preferred embodiment of the invention is described and explained in relation to FIGS. 7-14. Unless otherwise noted, the construction, materials and use of this embodiment of the invention are generally as described above for the prior preferred embodiments. It will also be understood and appreciated by those of skill in the art upon reading this disclosure that various features of this newly disclosed embodiment can have applicability to other embodiments previously disclosed, making such other modifications as may be recognized as desirable by those of skill in the art under particular circumstances in view of the teachings contained in this disclosure.

Referring to FIGS. 7-12, a preferred IV catheter introducer 210 of the invention preferably comprises plunger assembly 212, housing 214, retractable needle assembly 218 (further comprising plug 238 and retraction spring 280) insertable into housing 214, IV catheter assembly 216 attachable forwardly of housing 214, elastomeric grommet 258 disposed between housing 214 and IV catheter assembly 216, and removable cover 276. It should be appreciated, however, that use of a retraction spring and retractable needle are not required for use of elastomeric grommet 258 of the invention. Plunger assembly 212, housing 214, the body portions of retractable needle assembly 218, IV catheter assembly 216 and cover 276 are preferably all made of FDA approved, moldable polymeric materials, although it will be understood that different parts can comprise different materials. Elastomeric grommet 258 is preferably made of rubber, and is further discussed below.

Plunger assembly 212 has a forwardly extending end that is insertable into an opening in the back of housing 214. Plunger body 230 is hollow, with a rear opening surrounded by collar 222. End cap 220 is desirably insertable into frictional engagement with the inside of collar 222 (more visible in FIG. 13), although other similarly effective cap configurations can likewise be used, some of which are discussed above in relation to the previous embodiments. Annular rib 226 and circumferentially spaced, radially extending, elongate keys 228 are desirably provided to guide plunger assembly 212 as it advances forwardly into housing 214 during assembly. Keys 228 are preferably alignable with longitudinally directed keyways in the inside wall of housing 214 to maintain a preferred rotational alignment among plunger assembly 212 and retractable needle assembly 218 inside housing 214. This rotational alignment insures that the bevel of needle 246 is always upwardly facing as plunger assembly 212 is advance forwardly during insertion of needle 246 into a patient's vein.

Figures 7, 8:
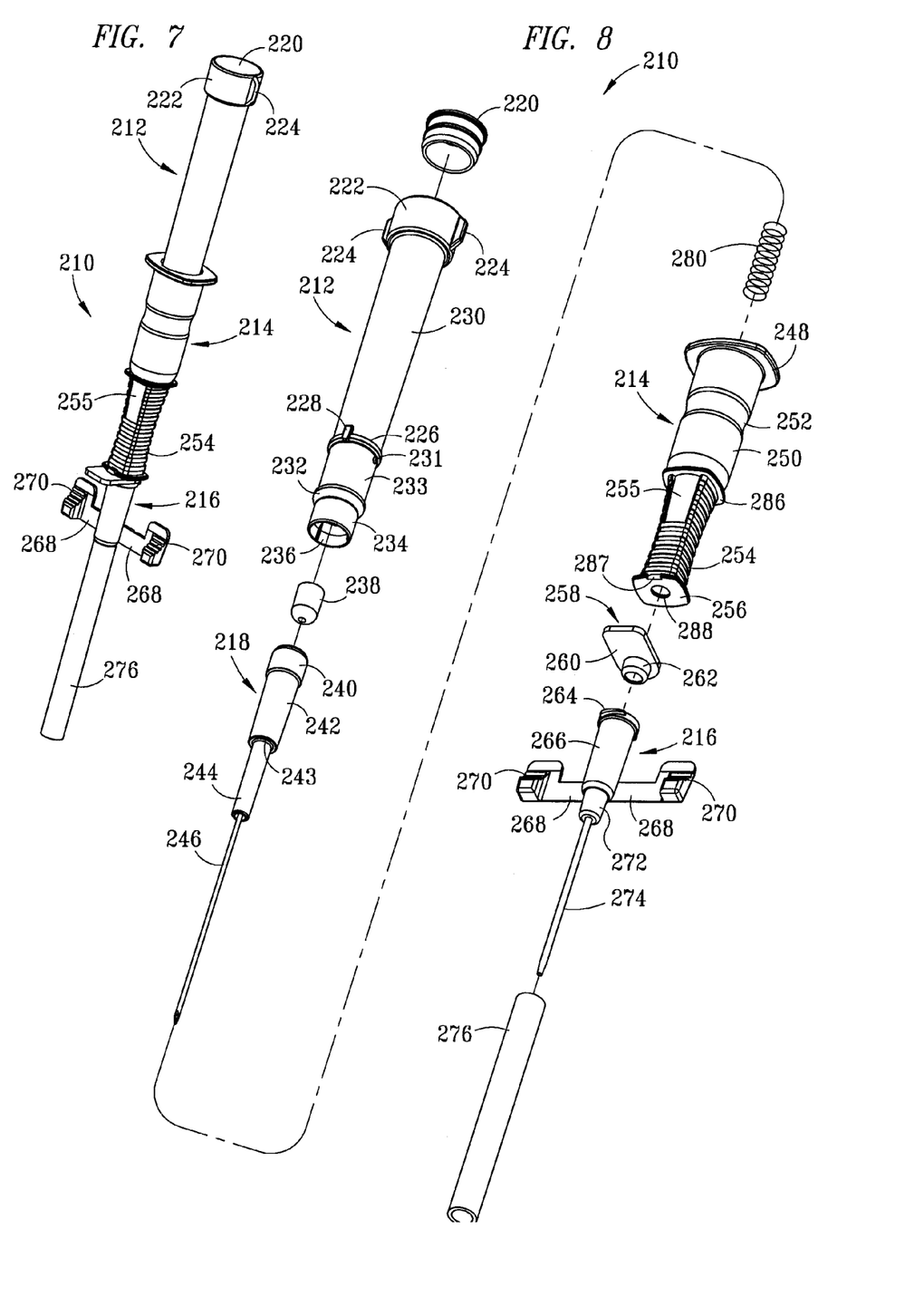
FIG. 7 is a simplified perspective view of a preferred IV catheter introducer as newly disclosed herein.
FIG. 8 is an exploded perspective view of the IV catheter introducer of FIG. 7.
Figure 9:
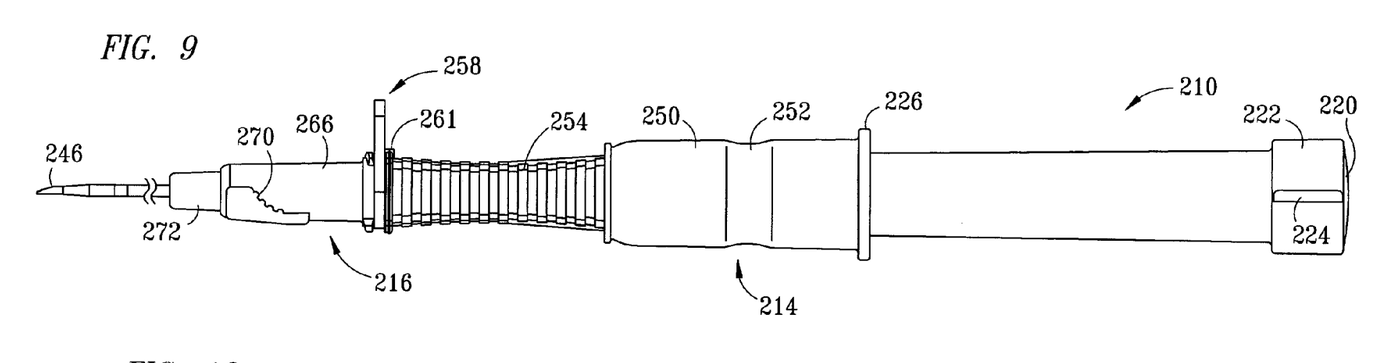
FIG. 9 is a front elevation view, partially broken away, of the IV catheter introducer of FIG. 7.
Figure 10:
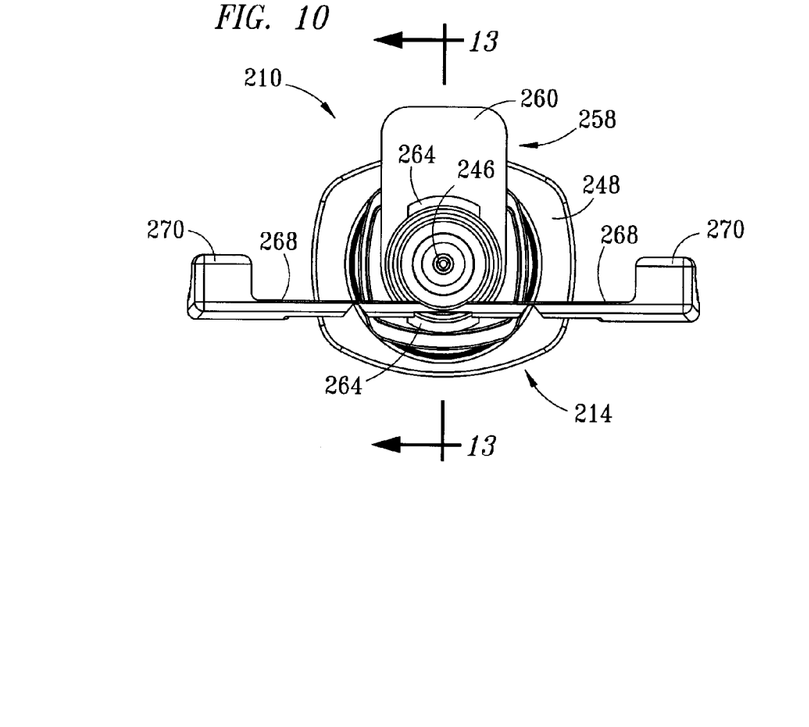
FIG. 10 is a left side view of the IV catheter introducer of FIG. 9.
Figure 11:
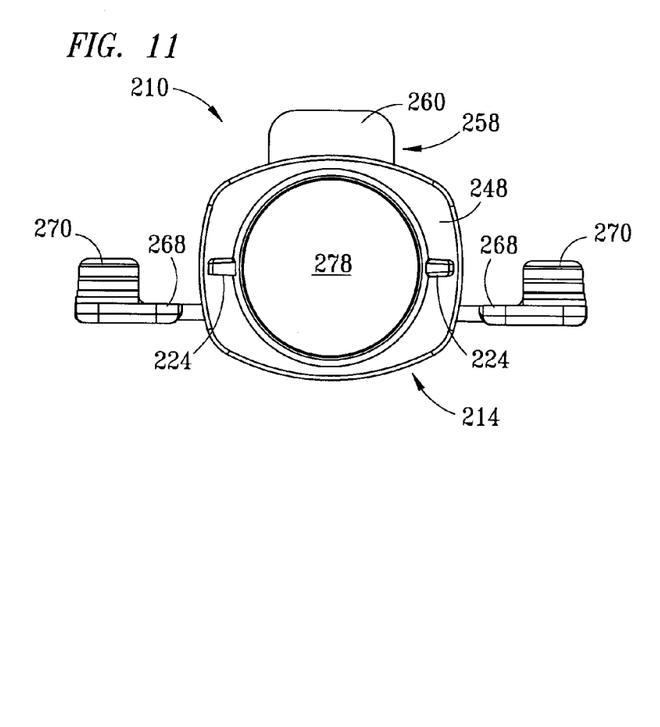
FIG. 11 is a right side view of the IV catheter introducer of FIG. 9.
Figure 12:
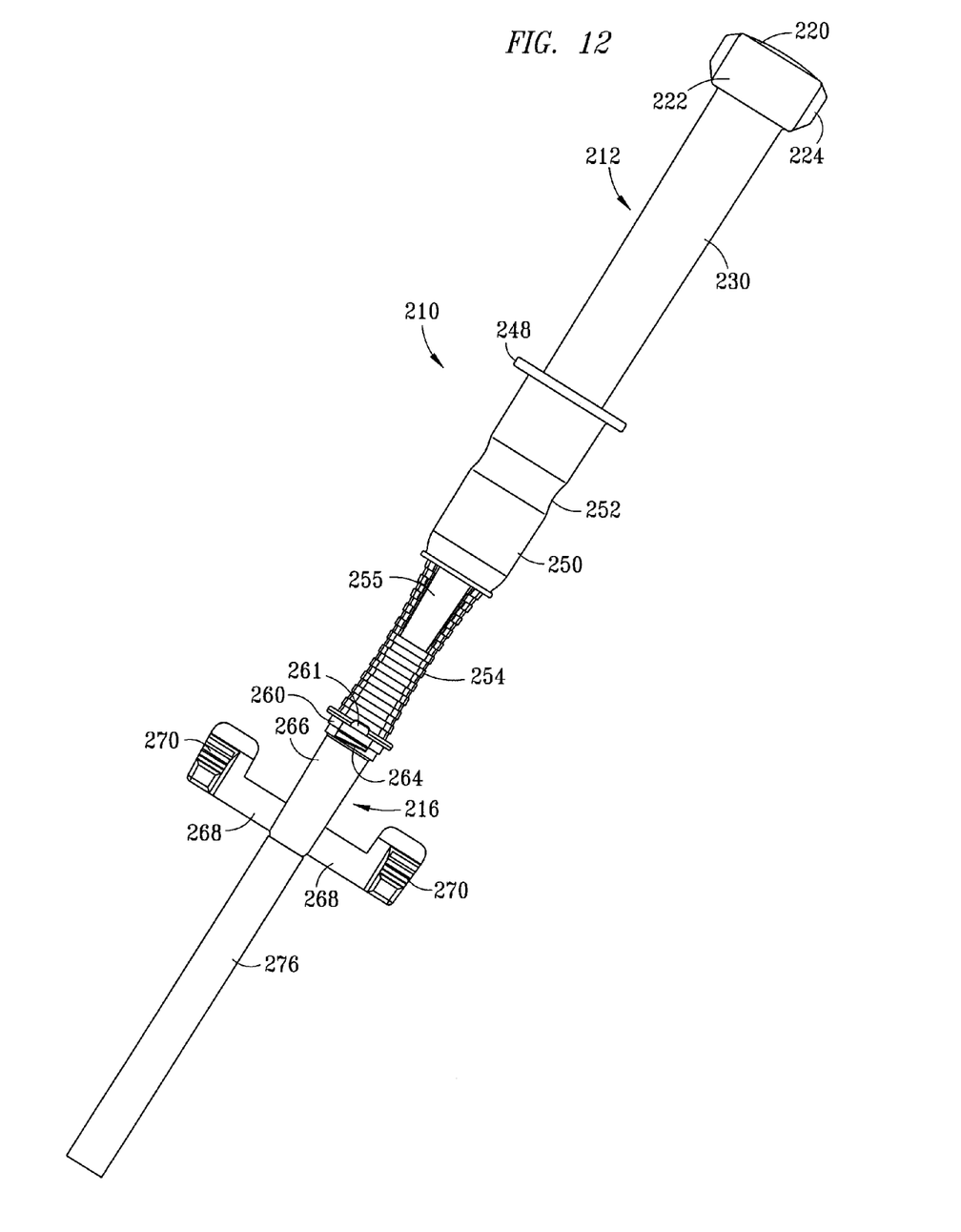
FIG. 12 is a top plan view of the IV catheter introducer of FIG. 9.
Figure 13:
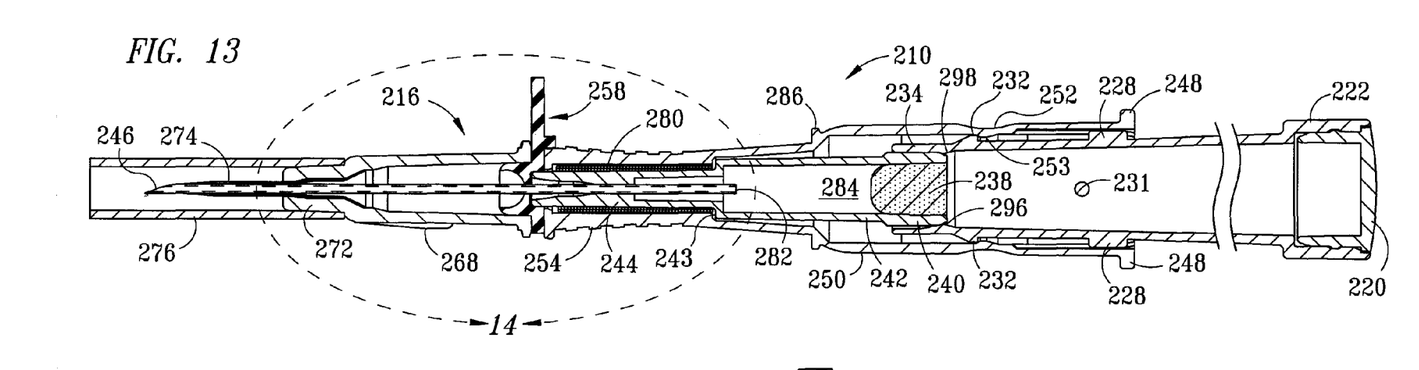
FIG. 13 is a cross-sectional view taken along line 13-13 of FIG. 10.

The forwardly extending, smaller-diameter front section 234 of plunger assembly 212 preferably comprises an opening 236 having a length and inside diameter sufficient to receive rearwardly facing end collar 240 of needle assembly 218, as discussed in greater detail below in relation to FIG. 13. Referring to FIGS. 8 and 13, inclined ramp 232 having a rearwardly facing, substantially square shoulder, is provided at the rear of body section 234. Ramp 232 slides past detent 252 in housing 214 during insertion of plunger assembly 212 into housing 214, but abutting engagement between the rearwardly facing shoulder and detent 252 subsequently resists rearward movement of plunger body 231 relative to housing 214 sufficiently to overpower the expansive spring force of compression spring 280 prior to retraction. Vent hole 231 is desirably provided in body 230 to reduce the likelihood of blood splattering forwardly out of IV catheter introducer 210 during retraction.

Figure 14:
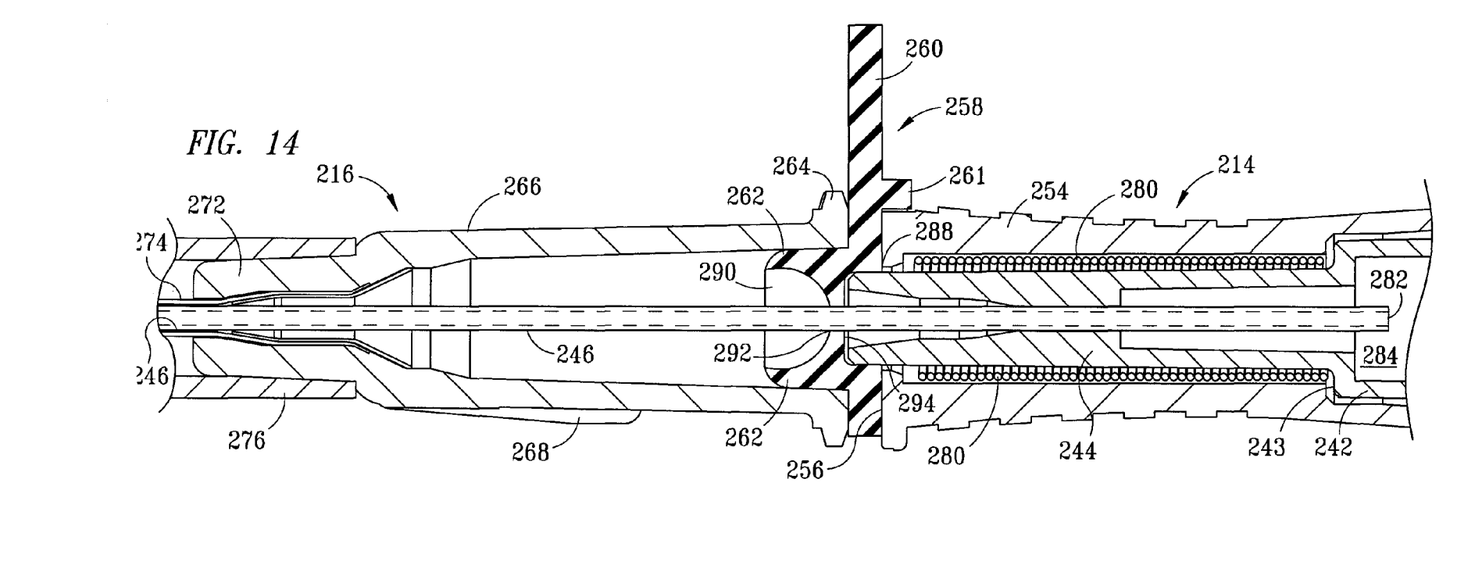
FIG. 14 is an enlarged, detail view of part of the IV catheter introducer of FIG. 13.

Needle assembly 218 preferably comprises end collar 240 and forwardly extending, reduced-diameter body sections 242 and 244 separated by annular shoulder 243, all of which are preferably molded out of substantially clear plastic. Body section 242 defines the wall of flash chamber 284 (FIG. 13) and body section 244 is preferably the needle holding section (FIGS. 13 and 14). Body section 244 has an outside diameter small enough to be insertable into compressible retraction spring 280. Annular shoulder 243 has sufficient width to abut the top of retraction spring 280 when installed inside housing 214 and to limit the rearward expansion of spring 280 prior to retraction. Needle 246 preferably has a beveled front end, a blunt rear end, and is insertable into, and held in fixed relation to, the body sections by any suitable means as previously disclosed. Needle 246 is preferably long enough to project forwardly from body section 244 a distance sufficient to be clinically effective for insertion through IV catheter assembly 216, and to project rearwardly through the interior of body sections 244, 242 and collar 240 so that blunt end 282 extends into flash chamber 284 (FIG. 14) inside body section 242. Plug 238, preferably made of a porous material as previously described, frictionally engages the inside wall of collar 240 and confines blood inside flash chamber 284 prior to retraction of needle 246.

Housing 214 preferably comprises a centrally disposed bore that is coaxially aligned with the centrally disposed bore through plunger 212, retractable needle assembly 218, and IV catheter assembly 218. The bore diameter is stepped inwardly between flange 286 (FIG. 8) and front flange 256 to provide a seating surface for annular shoulder 243 of retractable needle assembly 216 inside housing 214 (as seen in FIG. 13). Rear flange 248, flange 286 and front flange 256 are all desirably molded in a modified rectangular configuration to provide a substantially flat base for housing 214 when lying on a support surface. Referring to FIGS. 8 and 13, front flange 256 preferably further comprises an opening 288 having an inside diameter slightly greater than the outside diameter of body section 244 of retractable needle assembly 218 to permit the forwardly extending tip of body section 244 to pass through opening 288 for insertion into recess 294 in the back side of grommet 258. Molded ridges 254 are desirably provided for use as finger grips and substantially flat wall section 255 is desirably provided as a viewing window into underlying flash chamber 284 of retractable needle assembly 218. Housing 214 and the body of retractable needle assembly 218 are preferably molded from clear plastic to facilitate viewing of blood flowing into flash chamber 284 from the blunt end of needle 246. Annular detent 252 is provided in wall section 250 between rear flange 248 and flange 286 to cooperate with ramp 232 of plunger assembly 212 to resist the spring force being applied to annular shoulder 243 of retractable needle assembly 218 prior to retraction.

Elastomeric grommet 258, best seen in FIGS. 8 and 14, is preferably made of rubber and further comprises a substantially cylindrical, forwardly facing projection 262 having a concave arcuate recess 290, a rearwardly facing recess 294, preferably cylindrical, configured to receive the forwardly extending tip of body section 244 of retractable needle assembly 218, an upwardly extending tab 260 that identifies the top side of the catheter introducer (with the upwardly facing needle bevel), and a rearwardly projecting positioning tab 261 that is insertable into notch 287 or another similarly effective recess in front flange 256 of housing 214 to position grommet 258 rotationally with respect to housing 214. Digital pressure is desirably applied to upwardly extending tab 260 during insertion of catheter 274 into the vein and again when separating housing 214 from IV catheter assembly 216 prior to retraction of needle 246. Forwardly facing projection 262 preferably has an outside diameter that is sized to frictionally engage the inside wall of hub 266 of IV catheter assembly 216. Grommet 258 preferably comprises a thin elastomeric web (e.g., about 0.020 inches in thickness) disposed between recesses 290, 294 in which an aperture 292 is formed by insertion of needle 246 through the web during assembly of IV catheter introducer 210. Aperture 292 lightly engages the outside surface of needle 246 without constricting against needle 246 sufficiently to prevent full retraction of the needle by spring 280 following insertion of the catheter.

Grommet 258 can perform several valuable functions when incorporated as part of IV catheter introducer 210 of the invention. First, grommet 258 reduces the likelihood of unintentional separation of IV catheter assembly from the housing during shipping and handling prior to use. Second, aperture 292 acts as a guide for needle 246. Third, rearwardly facing recess 294 assures proper coaxial alignment of aperture 292 with the forwardly extending tip of body section 244 of needle assembly 218. Fourth, rearwardly projecting positioning tab 261 insures proper rotational alignment between grommet 258 and housing 214 so that tab 260 projects upwardly and not at some other rotational position relative to housing 214. Fifth, during insertion of needle 246, digital pressure can be applied against tab 260 while gripping ribs 254 of housing 214. Sixth, tab 260 of grommet 258 assists the user in separating housing 214 from hub 266 prior to retraction of the needle. Seventh, during withdrawal and retraction of needle 246, the slight contact between the thin web of grommet 258 and the outside of needle 246 wipes blood off the outside of needle 246. Eighth, during retraction, contact between the thin web of grommet 258 and the outside of needle 246 dampens the retraction force to slow down the needle and thereby reduce the likelihood of forward splatter in response to retraction. Ninth, grommet 258 impedes blood spillage out of the catheter hub after withdrawal of needle 246 from hub 266 and grommet 258.

Referring to FIGS. 7-12, IV catheter assembly 216 preferably comprises tapered tubular hub 266 comprising a connector collar 264 on the rearwardly facing end. Connector collar 264 is preferably configured for easy attachment to cooperatively configured end connectors of conventional, commercially available IV infusion sets, blood collection bags, or the like. A pair of diametrically opposed, laterally extending wings 268 are desirably attached to, or unitarily molded as part of, hub 266 to provide lateral support for IV catheter assembly 216 when placed in service on the body of a patient. Raised, textured finger pads 270 are preferably provided at or near the ends of wings 268 for use in stabilizing IV catheter assembly 216 during separation of hub 266 from housing 214 of IV catheter introducer 210 following retraction of needle 246. Catheter 274 is preferably a rubber or flexible plastic sheath having an inside diameter slightly greater than the outside diameter of needle 246, and a length sufficient to cover all but the beveled end of needle 246 when needle 246 is inserted through the catheter. Catheter 274 is preferably secured to the inside of tapered, forwardly extending tip 272 of IV catheter assembly 216 by any suitable means, such as, for example, those disclosed above in relation to the previous embodiment. Referring to FIGS. 8 and 13, cover 276, preferably made of molded plastic, has a length sufficient to protect the beveled tip of needle 246 prior to use and an inside diameter that frictionally engages the outside surface of tip 272.

Referring to FIGS. 13 and 14, following assembly of IV catheter assembly 210, needle 246 projects forwardly from catheter 274 and is protected during shipping and handling prior to use by removable cover 276 that frictionally engages the forwardly extending tip 272 of IV catheter assembly 216.

The inside of hub 266 frictionally engages the outside surface of cylindrical projection 262 of grommet 258. The forwardly extending end of body section 244 of retractable needle assembly 218 (FIG. 8) desirably extends into and frictionally engages the circumferentially extending sidewall of recess 294 of grommet 258. Needle 246 forms and passes through aperture 292 in the thin web section of grommet 258 and is disposed in fixed longitudinal relation to body section 244. Blunt end 282 of needle 246 desirably extends into flash chamber 284, which is visible through housing 214. Rear collar 240 of the needle holder is frictionally engaged by the inside surface of body section 234, and the rear of flash chamber 284 is blocked by frictionally engaged plug 238. Retraction spring 280 is compressed inside the longitudinally extending annular space between the back side of flange 256 of housing 214 and annular shoulder 243 of the needle holder, and is held in compression prior to retraction by contacting engagement between annular shoulder 232 of plunger assembly 212 (FIG. 8) and inwardly facing detent 253 of housing 214, and by contacting engagement between inwardly facing ridge 296 inside plunger assembly 212 and the rearwardly extending end portion of collar 240. Although retraction spring 280 is depicted as fully compressed in FIGS. 13 and 14, it should be appreciated that the annular space into which spring 280 is compressed is desirably slightly longer than the fully compressed length of spring 280 to provide a slight tolerance during manufacture and assembly so that complete compression is not required in order for the spring to fit within the annular space.

Following removal of cover 276, needle 246 and the forwardly extending tip of catheter 274 are desirably inserted into a vein by gripping ribs 254 of housing 214 and applying digital pressure to the back side of tab 260 of grommet 258. Once needle 246 has punctured the vein and catheter 274 is properly positioned inside the vein, digital pressure can be applied by one hand to finger pads 270 of wings 268 (FIG. 8) to hold hub 266 in place while housing 214 is separated from grommet 258 with the other hand while again applying digital pressure to tab 260. After separation has occurred and needle 246 has been withdrawn a short distance, such as from about ¼ to ½ inch, by pulling housing 214 backwards in relation to hub 266 and grommet 258, needle 246 can be retracted completely from catheter 274 by withdrawing plunger 212 relative to housing 214. Once plunger assembly 212 is withdrawn to an axial position where the rear of needle holder assembly 218 is not frictionally held by the inwardly facing wall of housing 214 and plunger assembly 212, spring 280 will expand, forcing needle holder assembly 218 rearwardly to a point where collar 240 is disposed inside plunger assembly 212 and needle 246 is retracted inside housing 214 behind grommet 258. Where no retraction spring is supplied, needle 246 is completely withdrawn by pulling housing 214 further backward relative to hub 266 and grommet 258.

Grommet 258 desirably remains in place in frictional engagement with the rearwardly facing end of hub 266 until medical personnel desire to connect hub 266 to an IV infusion apparatus, blood collection bag, or other medical device. Prior to such connection, aperture 292 in elastomeric grommet 258 has substantially closed following withdrawal or retraction of needle 246, and grommet 258 blocks any accidental spillage of blood from back end of hub 266.

Other alterations and modifications of the preferred embodiment described above will become apparent to those of ordinary skill in the art upon reading this disclosure, and it is intended that the scope of the invention disclosed herein be limited only by the broadest interpretation of the appended claims to which the inventor is legally entitled.

The invention claimed is:

1. An IV catheter introducer comprising in coaxial alignment a housing having a needle assembly seated therein with a body section and a needle projecting forwardly from the housing, a plunger assembly having a plunger tube slidably insertable into the housing, an IV catheter assembly having a flexible catheter attached to a rearwardly facing tubular hub, an elastomeric grommet disposed between and contacting a forward end of the housing and a rear end of the hub, and a removable cover disposed over part of the needle and catheter prior to use of the IV catheter introducer;

wherein the elastomeric grommet comprises a forwardly facing projection having an outside surface that frictionally engages an inside wall near the rear end of the hub, a rearwardly facing recess that receives and frictionally engages a forwardly extending tip of the body section, a thin elastomeric web disposed inside the elastomeric grommet forwardly of the rearwardly facing recess, and an upwardly extending tab identifying a top side of the catheter introducer that corresponds to a beveled side of the needle.

2. The IV catheter introducer of claim 1, further comprising a needle retraction spring.

3. The IV catheter introducer of claim 1 wherein the elastomeric grommet is made of rubber.

4. The IV catheter introducer of claim 1 wherein the forwardly facing projection of the elastomeric grommet is substantially cylindrical.

5. The IV catheter introducer of claim 1 wherein the needle is inserted axially through the thin elastomeric web during assembly.

6. The IV catheter assembly of claim 5 wherein the thin elastomeric web wipes the outside of the needle as the needle is withdrawn from the IV catheter assembly and from the elastomeric grommet following use.

7. The IV catheter assembly of claim 1 wherein the elastomeric grommet impedes blood flow rearwardly out of the hub following insertion of the catheter, separation of the housing from the elastomeric grommet, and withdrawal of the needle from the elastomeric grommet.

8. The IV catheter assembly of claim 1 wherein the elastomeric grommet comprises a rearwardly facing positioning tab that cooperatively engages a notch or recess in the housing to rotationally align the grommet and housing.

9. The IV catheter introducer of claim 1, further comprising a pair of laterally extending wings.

10. The IV catheter introducer of claim 9 wherein the wings are attached to the hub.

11. The IV catheter introducer of claim 10 wherein the wings each have raised finger pads.

* * * * *